US009055905B2

(12) United States Patent
Watkins et al.

(10) Patent No.: US 9,055,905 B2
(45) Date of Patent: Jun. 16, 2015

(54) APPARATUSES AND METHODS OF DETERMINING IF A PERSON OPERATING EQUIPMENT IS EXPERIENCING AN ELEVATED COGNITIVE LOAD

(75) Inventors: Michael L. Watkins, Richland, WA (US); Paul Edwin Keller, Richland, WA (US); Ivan A. Amaya, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 613 days.

(21) Appl. No.: 13/414,107

(22) Filed: Mar. 7, 2012

(65) Prior Publication Data

US 2012/0235819 A1    Sep. 20, 2012

Related U.S. Application Data

(60) Provisional application No. 61/454,162, filed on Mar. 18, 2011.

(51) Int. Cl.
*G08B 23/00* (2006.01)
*G05D 1/00* (2006.01)
*A61B 5/18* (2006.01)
*B60W 40/09* (2012.01)
*B60W 50/00* (2006.01)

(52) U.S. Cl.
CPC .................. *A61B 5/18* (2013.01); *B60W 40/09* (2013.01); *B60W 2050/0089* (2013.01); *B60W 2530/14* (2013.01)

(58) Field of Classification Search
CPC .......... G08B 23/00; G06F 19/00; G05D 7/00; G09G 5/00
USPC ........................................................ 340/573.1
See application file for complete search history.

(56) References Cited

U.S. PATENT DOCUMENTS

| 6,061,610 A * | 5/2000 | Boer ................................. 701/1 |
| 6,157,913 A | 12/2000 | Bernstein |
| 6,466,232 B1 * | 10/2002 | Newell et al. ................. 715/700 |
| 6,580,973 B2 * | 6/2003 | Leivian et al. .................... 701/1 |
| 6,873,911 B2 * | 3/2005 | Nishira et al. ................ 701/301 |
| 7,292,152 B2 | 11/2007 | Torkkola |
| 7,565,230 B2 | 7/2009 | Gardner |

(Continued)

FOREIGN PATENT DOCUMENTS

WO        02/33529 A2    4/2002

OTHER PUBLICATIONS

International Search Report and Written Opinion, PCT/US12/28147, dated May 31, 2012.

(Continued)

*Primary Examiner* — Jennifer Mehmood
*Assistant Examiner* — John Mortell
(74) *Attorney, Agent, or Firm* — Buchanan Nipper (57) ABSTRACT

A method of, and apparatus for, determining if a person operating equipment is experiencing an elevated cognitive load, wherein the person's use of a device at a first time is monitored so as to set a baseline signature. Then, at a later time, the person's use of the device is monitored to determine the person's performance at the second time, as represented by a performance signature. This performance signature can then be compared against the baseline signature to predict whether the person is experiencing an elevated cognitive load.

25 Claims, 5 Drawing Sheets

(56) References Cited

U.S. PATENT DOCUMENTS

| | | | |
|---|---|---|---|
| 7,766,827 B2 * | 8/2010 | Balkin et al. | 600/300 |
| 7,856,203 B2 | 12/2010 | Lipovski | |
| 8,190,319 B2 * | 5/2012 | Syed et al. | 701/22 |
| 2003/0046401 A1 | 3/2003 | Abbott | |
| 2004/0037236 A1 | 2/2004 | Massey | |
| 2004/0222892 A1 | 11/2004 | Balaban | |
| 2007/0219672 A1 | 9/2007 | Fehr | |
| 2008/0299959 A1 | 12/2008 | Geyer | |
| 2009/0298482 A1 | 12/2009 | Yen | |
| 2010/0113073 A1 | 5/2010 | Schlesener | |
| 2010/0217097 A1 | 8/2010 | Chen | |
| 2011/0009107 A1 | 1/2011 | Guba | |

OTHER PUBLICATIONS

National Highway Transportation Safety Administration (NHTSA), "Examination of Driver Distraction as Recorded in NHTSA Databases," Report No. DOT HS 811 216, Sep. 2009.

Boyle, J.M. and Lampkin, C., "Motor Vehicle Occupant Safety Survey, vol. 4, Crash Injury and Emergency Medical Services Report," Report No. DOT HS 810 977, Dec. 2008.

Exec. Order No. 13513, "Federal Leadership on Reducing Text Messaging While Driving," 74 Fed. Reg. 51225 (2009).

Watkins, M.L., et al., "Intelligent Device Applications for Real-Time Characterization of Cognitive Loading: The Implications for Distracted Driving," 2nd International Symposium on Naturalistic Driving by the Virginia Transportation Research Institute (VTTI), Aug. 31, 2010.

Wickens, C.D., "Multiple Resources and Mental Workload", Human Factors: The Journal of the Human Factors and Ergonomics Society, vol. 50, No. 3, Jun. 2008, pp. 449-455.

National Highway Transportation Safety Administration (NHTSA), "Driver Strategies for Engaging in Distracting Tasks Using In-Vehicle Technologies," Report No. DOT HS 810 919 (2008).

Strayer, D. L. & Johnston, W.A., "Driven to Distraction: Dual-task studies of simulated driving and conversing on a cellular telephone," Psychological Science, vol. 12, No. 6, Nov. 2001, pp. 462-466.

Nakayama, et. al., "Development of a Steering Entropy Method for Evaluating Driver Workload," SAE Technical Paper 1999-01-0892 (1999).

Boer, E.R., "Behavioral Entropy as a Measure of Driving Performance," 2001 Driving Assessment Conference, Aspen, Colorado, Aug. 14-17, 2001.

Boer, E.R., "Steering Entropy Revisited," Proceedings of the Third International Driving Symposium on Human Factors in Driver Assessment, Training and Vehicle Design, pp. 25-32 (2005).

Strayer, D.L. and Drews, F.A., "Profiles in driver distraction: Effects of Cell Phone Conversations on Younger and Older Drivers," Human Factors, vol. 46, No. 4, Winter 2004, pp. 640-649.

Strayer, D.L., Drews, F.A., and Johnston, W.A., "Cell phone-induced failures of visual attention during simulated driving," Journal of Experimental Psychology: Applied, vol. 9, No. 1, pp. 23-32 (2003).

Kersloot, T., et al., "Steering Entropy as a Measure of Impairment," European Conference of Transport Research Institutes, Young Researchers Seminar 2003, Session 6.

Zahid, et al., "Keystroke-based User Identification on Smart Phones," Proceedings of the 12th International Symposium on Recent Advances in Intrusion Detection, RAID 2009, LNCS 5758, pp. 224-243.

Delahaye, D., and Puechmorel, S., "Air Traffic Complexity: Towards Intrinsic Metrics," 3rd USA/Europe Air Traffic Management R&D Seminar, Napoli, Jun. 13-16, 2000.

\* cited by examiner

APPARATUSES AND METHODS OF DETERMINING IF A PERSON OPERATING EQUIPMENT IS EXPERIENCING AN ELEVATED COGNITIVE LOAD

PRIORITY/CROSS-REFERENCE TO RELATED APPLICATIONS

This application claims the benefit of U.S. Provisional Application No. 61/454,162, filed 18 Mar. 2011, the disclosure of which is incorporated by reference.

STATEMENT REGARDING FEDERALLY SPONSORED RESEARCH OR DEVELOPMENT

This invention was made with Government support under Contract DE-AC0576RLO1830 awarded by the U.S. Department of Energy. The Government has certain rights in the invention.

TECHNICAL FIELD

The disclosure generally relates to a method of determining if a person operating equipment is experiencing an elevated cognitive load. Particular embodiments of equipment relate to messaging devices, wireless communication devices, portable computing devices, and safety monitoring devices.

BACKGROUND

A person's "cognitive load" is the degree to which the person's working memory is engaged in processing information. The more working memory is used, the higher the cognitive load. The higher a person's cognitive load, the greater the chances that "distracted operating" will impact the person's performance in operating a piece of equipment.

For instance, a person driving an automobile while operating a hand-held electronic device (e.g., text messaging on a cellular device) will experience an elevated cognitive load as the person tries to operate both the automobile (the equipment) and the hand-held electronic device at the same time. This impact on performance can be generally referred to as one type of "distracted driving."

According to the National Highway Traffic Safety Administration (NHTSA), "distracted driving" is a dangerous epidemic on America's roadways, as evidenced by the fact that in 2009 alone, it is estimated that nearly 5,500 people were killed, and 450,000 people were injured in distracted driving crashes.

"Distracted operating" isn't limited to distractions caused by the utilization of hand-held electronic devices while operating equipment. Many other activities, events and situations can elevate a person's cognitive load. For instance, other activities, events and/or situations which can elevate a person's cognitive load include, but are not limited to, stress, mood, grief, the person's physical and/or mental health, the person's age, the person's maturity, cigarette smoking, eating, drinking, emergencies, sleepiness, weather conditions, the presence of hazards, "multi-tasking" (e.g., operating the equipment while also utilizing social media, playing games, watching television, listening to music, and/or talking on the telephone).

"Impaired operating" (e.g., under the influence of alcohol, under the influence of illegal drugs, under the influence of prescription drugs) is likewise a concern. For instance, the impact of alcohol on a person's performance in operating an automobile is well known.

Therefore, a need exist for methods of, and apparatuses for, determining if a person operating equipment is experiencing an elevated cognitive load.

SUMMARY OF THE DISCLOSURE

Several exemplary methods of determining if a person operating equipment is experiencing an elevated cognitive load are described herein.

An exemplary method of determining if a person operating equipment is experiencing an elevated cognitive load while using a device comprises a series of steps. The first step is collecting a first set of data related to the person's operation of the device at a first time when the person is not experiencing an elevated cognitive load. The second step is processing the first set of data to establish a baseline signature. The third step is collecting a second set of data related to the person's operation of the device at a second time. The fourth step is processing the second set of data to establish a performance signature. The fifth step is comparing the performance signature to the baseline signature to determine whether the person is experiencing an elevated cognitive load at the second time. This exemplary method can include a number of optional steps.

The first optional step is triggering a response if the person is experiencing an elevated cognitive load. The "response" in this optional step can be applying a limitation to the person's use of the device and/or equipment. The "response" in this optional step can be reporting that the person was experiencing an elevated cognitive load while operating the device and/or equipment at the second time. The "response" in this optional step can be providing feedback to the person regarding the existence of an elevated cognitive load while operating the device and/or equipment at the second time.

A second optional step is collecting a third set of data from a motion detector. A sub-step to this second optional step is processing the third set of data to establish a second performance signature, wherein the second performance signature relates to movement. A sub-step to this sub-step is triggering a response if the person is experiencing an elevated cognitive load and the person is moving.

In a third optional step, the collection of first and second sets of data comprises the step of measuring behavioral biometric data relating to the person's operation of the device. In an optional sub-step to this fourth optional step, the measurement of behavioral biometric data comprises measuring keystroke dynamic data related to the person's operation of the device. Optionally, the device in this fourth optional step is a messaging device. In an optional sub-step to the fourth optional step, the measurement of behavioral biometric data comprises measuring the person's speech patterns related to the person's operation of the device.

A fourth optional step comprises triggering a response if the person is experiencing an elevated cognitive load, and wherein the steps of collecting a first set of data and collecting a second set of data comprise measuring behavioral biometric data relating to the person's operation of the device, and further wherein the measurement of behavioral biometric data comprises measuring keystroke dynamic data related to the person's operation of the device.

Another exemplary method of determining if a person operating equipment is experiencing an elevated cognitive load comprises the steps of: collecting a first set of data related to the person's operation of a device at a first time when the person is not experiencing an elevated cognitive load; processing the first set of data to establish a baseline signature; collecting a second set of data related to the person's operation of the device at a second time; processing the second set of data to establish a performance signature; comparing the performance signature to the baseline signature to determine whether the person is experiencing an elevated cognitive load at the second time; and triggering a response if the person is experiencing an elevated cognitive load.

Optionally, the response is selected from the group consisting of applying a limitation to the person's use of the device and/or equipment, reporting that the person was experiencing an elevated cognitive load while operating the device and/or equipment at the second time, and providing feedback to the person regarding the existence of an elevated cognitive load while operating the device and/or equipment at the second time. Further optionally, the method comprises the steps of: collecting a third set of data from a motion detector; processing the third set of data to establish a second performance signature, wherein the second performance signature relates to movement; and triggering a response if the person is experiencing an elevated cognitive load and the person is moving.

Another exemplary method of determining if a person operating equipment is experiencing an elevated cognitive load comprises the steps of: measuring behavioral biometric data relating to the person's operation of a device to collect a first set of data related to the person's operation of the device at a first time when the person is not experiencing an elevated cognitive load; processing the first set of data to establish a baseline signature; measuring behavioral biometric data relating to the person's operation of the device to collect a second set of data related to the person's operation of the device at a second time; processing the second set of data to establish a performance signature; comparing the performance signature to the baseline signature to determine whether the person is experiencing an elevated cognitive load at the second time; and triggering a response if the person is experiencing an elevated cognitive load. Optionally, the device is a messaging device. Optionally, the measurement of behavior biometric data comprises measuring keystroke dynamic data related to the person's operation of the messaging device.

Apparatuses utilized to determine if a person operating equipment is experiencing an elevated cognitive load are also described.

Additional understanding of the devices and methods contemplated and/or claimed by the inventors can be gained by reviewing the detailed description of exemplary devices and methods, presented below, and the referenced drawings.

DEFINITIONS

The following description and the referenced drawings provide illustrative examples of that which the inventors regard as their invention. As such, the embodiments discussed herein are merely exemplary in nature and are not intended to limit the scope of the invention, or its protection, in any manner. Rather, the description and illustration of these embodiments serve to enable a person of ordinary skill in the relevant art to practice the invention.

The use of "e.g.," "etc," "for instance," "in example," and "or" and grammatically related terms indicates non-exclusive alternatives without limitation, unless the context clearly dictates otherwise.

The use of "first step," "second step," indicate a preferred order of steps, but does not dictate that the "first" step must be performed before the "second" step in every exemplary method and apparatus. For instance, in an exemplary method the performance signature could be calculated before the baseline signature is calculated.

The use of "including" and grammatically related terms means "including, but not limited to," unless the context clearly dictates otherwise.

The use of the articles "a," "an," and "the" are meant to be interpreted as referring to the singular as well as the plural, unless the context clearly dictates otherwise. Thus, for example, reference to "a motion detector" includes two or more such motion detector, and the like.

The use of "set of data" means "collection of data, from one or more data sources," unless the context clearly dictates otherwise.

The use of "optional" and grammatically related terms means that the subsequently described element, event or circumstance may or may not be present/occur, and that the description includes instances where said element, event or circumstance occurs and instances where it does not.

The use of "preferred" and grammatically related terms means that a specified element or technique is more acceptable than another, but not that such specified element or technique is a necessity, unless the context clearly dictates otherwise.

The use of "exemplary" means "an example of" and is not intended to convey a meaning of an ideal or preferred embodiment.

The use of "cognitive load" means "the degree to which working memory is engaged in processing information," unless the context clearly dictates otherwise. The more working memory is used, the higher the cognitive load.

The use of "behavior biometric data" means "biometric data related to an individual's behavior (e.g., keystroke dynamics, speech patterns, signature verification)" unless the context clearly dictates otherwise.

The use of "keystroke dynamic data" means "behavior biometric data which focuses on the motion made by a person in operating equipment," unless the context clearly dictates otherwise. Keystroke dynamic data is not limited to utilization of a keyboard, for instance, examples of keystroke dynamic data includes, but is not limited to, information regarding when each key on a keyboard was pressed and when it was released as a person is typing using a keyboard, information regarding motions made when a person is entering information using a gesture-based input method, information regarding motions made when a person is signing (signature) a document.

The use of "motion detector" means "a method or apparatus for detecting the relative motion of a person, device, equipment, and/or object," unless the context clearly dictates otherwise. Examples of motion detectors include, but are not limited to: position measurement using a satellite (e.g., global positioning satellite (GPS)), accelerometers, tilt sensors, position sensors, vibration sensors, variations in velocity vector and acceleration signal, vehicle data sensors (e.g., throttle sensors, brake sensors, steering sensors), multilateration, and speed sensors. A motion detector may generate a motion sensor signal.

The use of "messaging device" means "a communication device for creating and sending information and messages across a communication network," unless the context clearly dictates otherwise. Examples of messaging devices include, but are not limited to, mobile telephones, cellular telephones, satellite telephones, pagers, tablet computers, laptop computers, networked personal computers, digital device, portable entertainment devices, wireless communication devices, safety monitoring devices, and personal digital assistants.

The use of "messages" means "electronically transmitted communications," unless the context clearly dictates otherwise. Examples of messages include, but are not limited to, text messages (e.g., Short Message Service (SMS) messages, Multimedia Messaging Service (MMS) messages, J-Phone SkyMail messages, NTT Docomo's Short Mail messages), instant messaging messages (e.g., iMessage, AOLIM, ICQ, Skype), social networking messages (e.g., Facebook, Twitter), mobile application messages, pager messages, and electronic mail messages.

The use of "vehicle" means "any means by which a person and/or goods may be transported (e.g., automobiles, trucks, tractor-trailers, motorcycles, bicycles, watercraft, aircraft, trains)," unless the context clearly dictates otherwise.

The use of "equipment" is to be construed in a broad, expansive manner, including any such devices or other objects without limitation. Examples of "equipment" include, but are not limited to, mechanical equipment, electrical equipment, industrial equipment, office equipment, factory equipment, vehicles, machinery, hardware, software, etc.

The use of "entropy" means "entropy as applied in the field of information theory (e.g., Shannon Entropy, Rényi entropy, Tsallis entropy)," unless the context clearly dictates otherwise.

DETAILED DESCRIPTION

Several exemplary methods of, and apparatus for, determining if a person operating equipment is experiencing an elevated cognitive load are described herein.

If a person is experiencing an elevated cognitive load while operating a piece of equipment, the chances that the person will make one or more errors in the operation of the equipment are increased. Further, outside factors (other than distracted operation) can impact a person's performance while operating a piece of equipment, for instance, being ill, or being injured. Depending upon the error made, the lives and well-being of people (including the person) could be at stake, as well as valuable property (including the equipment) possibly being damaged or destroyed.

In the exemplary methods and apparatuses, a person's use of a device at a first (control) time is monitored (and a first set of data is collected) so as to set a baseline signature.

Alternatively, the baseline signature could not be based on monitoring the person's use of a device at a first (control) time, but could instead be based upon a standard (e.g., based upon data collected from many users) or an estimated value.

Then, at a later time, the person's use of the device is monitored (and a second set of data is collected) to determine the person's performance at the second time, as represented by a performance signature.

This performance signature can then be compared against the baseline signature to predict whether the person is experiencing an elevated cognitive load. For instance, if the value of the performance signature exceeds a baseline signature by a certain value or percent, an elevated cognitive load can be predicted. In another example, the comparison comprises a change in Shannon Entropy ($\Delta E$=performance signature–baseline signature).

If an elevated cognitive load is detected, a response (such as disabling the device) can be taken to encourage the person to focus on another task (such as operating a vehicle). This response could be triggered automatically, or could be triggered at a later time.

A first exemplary response to the detection of an elevated cognitive load is applying a limitation to the person's use of the device. Examples of limitations include, but are not limited to, certain functions of the device being disabled, the device itself being temporarily disabled (e.g., powered down, locked, put into a "sleep" mode), the device being permanently disabled, and revocation of the user's authorization to use the device. By limiting or blocking further use of the device, one of the factors resulting in the person's elevated cognitive load is eliminated, thereby allowing the person's cognitive load to decrease to "normal." The limitation on use could exist for a predetermined period of time (e.g., thirty minutes), until the user takes a separate step (calling a phone number to reactivate), contacting a supervisor to override the limitation, requiring a third party to override the limitation, etc.

A second exemplary response to the detection of an elevated cognitive load is applying a limitation to the person's use of the equipment. For instance, the equipment could be disabled (e.g., powered down, locked, put into a "sleep" mode), or the user's authorization to use the equipment could be revoked, thereby preventing further use by the person. By limiting or blocking further use of the equipment, errors that might result from distracted use of the equipment are prevented. Once the person's elevated cognitive load returns to "normal," the person's authorization to use the equipment could be restored. The limitation on use could exist for a predetermined period of time (e.g., thirty minutes), until the user takes a separate step (calling a phone number to reactivate), contacting a supervisor to override the limitation, requiring a third party to override the limitation, etc.

A third exemplary response to the detection of an elevated cognitive load is reporting that the person was experiencing an elevated cognitive load while operating the device and/or equipment at the second time. This reporting could be done be instantaneously (e.g., as an alarm or other warning provided to the person), contemporaneously with the detection, and/or some time later. The reporting could be provided to a third party, such as a parent, an employer, an insurance company, or the authorities (e.g., police, emergency response team). The reporting could also be feedback provided to the person (e.g., warning lights, sounds, visible warning, email notices, etc.)

Any suitable collection, measurement, or sensing process and/or apparatus can be utilized to collect the first set of data and/or the second set of data, and a skilled artisan will be able to select an appropriate collection process and/or apparatus in a particular embodiment based on various considerations, including the device in question, the equipment/device in question, and the person in question, among other considerations.

In one exemplary method, the first and second sets of data are collected through monitoring the person's use of the device, and collecting use data. The data collected could include behavioral biometric data relating to the person's operation of the device, for instance, logging keystroke dynamic data related to the person's operation of the device where the device has an input device (e.g., keyboard, touch screen, mouse) which is utilized by the person.

For instance, where the device has a keyboard, keystroke dynamic data related to the person's use of the keyboard could comprise logging one or more of: the time between sequentially depressing horizontally adjacent keys, time between sequentially depressing vertically adjacent keys, the time between sequentially depressing adjacent diagonal keys, the time between sequentially depressing non-adjacent horizontal keys, the time between sequentially depressing non-adjacent vertical keys, the time between sequentially depressing non-adjacent diagonal keys, the timing/frequency of the use of the backspace or other "delete" key, the timing/frequency of the repeated depression of the same key(s), the word length, timing/frequency of the utilization of extra (unneeded) spaces, and/or the time difference between pressing a key and releasing it.

For instance, in the case of a keyless "touch screen" user interface, which offer virtual touch keys or swipe texting options, the "keystroke" dynamic data could include intended key selection as the user drags their finger across the touch screen, e.g., time sequencing of the characters selected, and/or the actual displacement patterns traced out in 3 dimensions (two dimensions in space and one in time).

The data collected could include positioning information regarding how the device is positioned during use (e.g., how the person is holding the device (e.g., one-handed, two-handed), how the person has positioned the device (e.g., horizontally, vertically), how the person has oriented the device).

Other sensor data could be utilized, for instance, data regarding whether the person is operating (or in a position to operate) the equipment, electromagnetic or acoustic signatures from sources such as the vehicle operator cockpit, etc.

Figure 1:
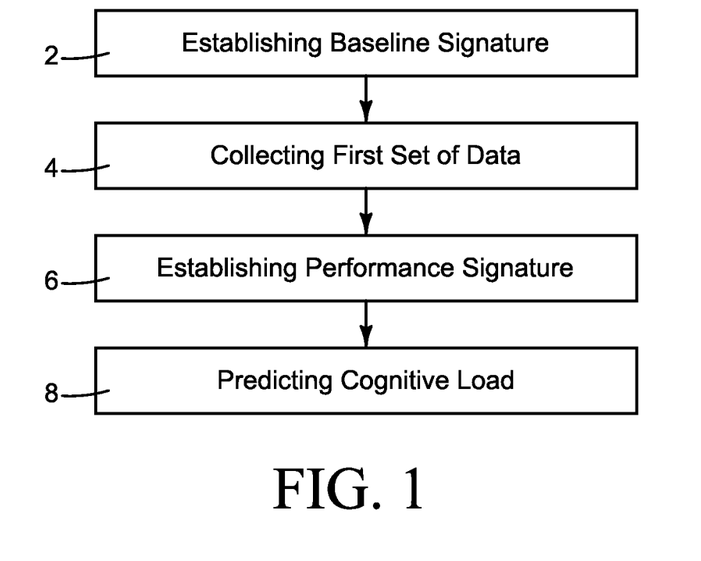
FIG. 1 is a flowchart illustrating a first exemplary method of determining if a person operating equipment is experiencing an elevated cognitive load.

Referring initially to FIG. 1, illustrated is an exemplary method of determining if a person operating equipment is experiencing an elevated cognitive load while using a device. The method comprising a series of steps.

At a first step 2, a baseline signature is set or calculated. This baseline signature representing the person's performance (use of the device) when not experiencing an elevated cognitive load. The baseline signature used as the baseline (control) against which the person's later performance (use of the device) is compared to determine if the person is experiencing an elevated cognitive load. This baseline signature may be estimated. This baseline signature may be based upon measured data regarding the person's performance when not experiencing an elevated cognitive load.

The baseline signature could be developed using randomness measures, likely relating to Shannon entropy, such as Rényi entropy, or Tsallis entropy, employing Bayesian statistics to provide the "a prior" probability density functions.

At a second step 4, a first set of data is collected. This first set of data is related to the person's operation of the device. At a third step 6, the first set of data is processed to establish a performance signature. At a fourth step 8, the performance signature is compared to the baseline signature to determine the probability (predict) whether the person is experiencing an elevated cognitive load. This comparison can include a determination of whether the performance signature is within or outside of a predesignated range, whether the performance signature is greater (or less) than the baseline signature, whether the difference between the performance signature and the baseline signature is within or outside a predesignated range, etc.

In one exemplary manner of processing the first set of data (measured in bits), the entropy signature is created according to the following equation ("Equation A"):

$$E = \sum_{i=1}^{N} p(t_i)\ln(p(t_i))$$

where N are all the possible values contained in the event stream (the number of bins used to form the histogram), and $p(t_i)$ is the estimated probability of a discrete event occurring. The binning process combines continuous events into discrete representations. In the case of this method, the number of bins can be adjusted to produce an optimal estimate of entropy.

In a second exemplary manner of processing the first set of data (measured in bits), the entropy signature is created according to the following equation ("Equation B"):

$$E_\alpha = \frac{1}{1-\alpha}\ln\left(\sum_{i=1}^{N} p^\alpha(t_i)\right)$$

$$(\alpha \geq 0, \alpha \neq 1)$$

In a first exemplary manner of processing a second set of data (measured in bits), an entropy signature is created according to the Equation A. In a second exemplary manner of processing a second set of data (measured in bits), an entropy signature is created according to the Equation B.

Figure 2:
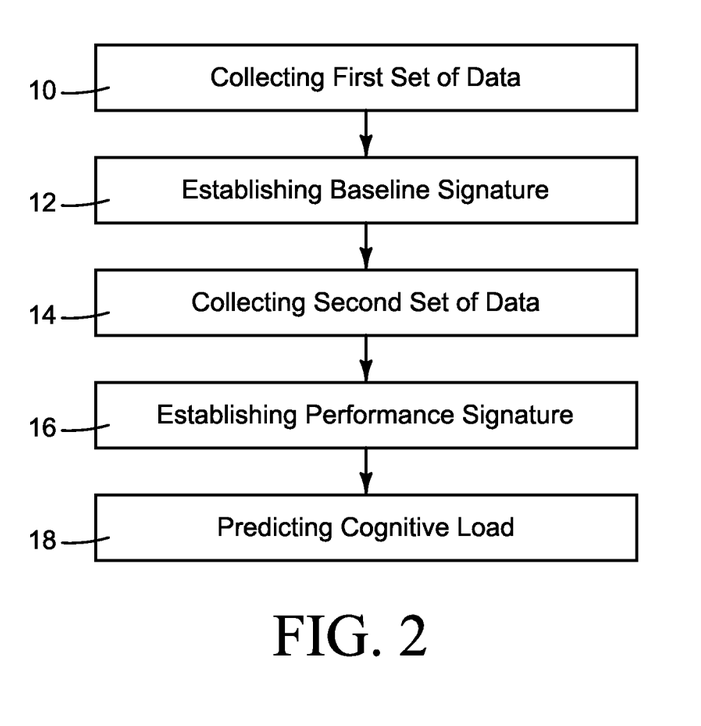
FIG. 2 is a flowchart illustrating a second exemplary method of determining if a person operating equipment is experiencing an elevated cognitive load.

Referring to FIG. 2, illustrated is an exemplary method of determining if a person operating equipment is experiencing an elevated cognitive load while using a device. The method comprising a series of steps.

At a first step 10, a first set of data is collected. This first set of data relating to the person's operation of the device itself. This first set of data is used to set a baseline (control) against which the person's later performance is compared against to determine if the person is experiencing an elevated cognitive load.

Because the first set of data is used to set a baseline performance, it is preferred that the first step be performed at a first time when the person is known to not be experiencing an elevated cognitive load, or when the person is less likely to be experiencing an elevated cognitive load. Alternatively, the first set of data could be selected to filter out any elevated cognitive load experienced. Alternatively, the first set of data could be large enough that it is not necessary to determine whether the person is or is not experiencing an elevated cognitive load to select the first set of data used to set a baseline performance.

At a second step 12, the first set of data is processed to establish a baseline signature. This baseline signature representing the person's performance (use of the device) when not experiencing an elevated cognitive load. The baseline signature is used as the baseline (control) against which the person's later performance (use of the device) is compared to determine if the person is experiencing an elevated cognitive load.

In one exemplary manner of processing the first set of data (measured in bits), the entropy signature is created according to the following equation ("Equation A"):

$$E = \sum_{i=1}^{N} p(t_i)\ln(p(t_i))$$

where N are all the possible values contained in the event stream (the number of bins used to form the histogram), and $p(t_i)$ is the estimated probability of a discrete event occurring. The binning process combines continuous events into discrete representations. In the case of this method, the number of bins can be adjusted to produce an optimal estimate of entropy.

In a second exemplary manner of processing the first set of data (measured in bits), the entropy signature is created according to the following equation ("Equation B"):

$$E_\alpha = \frac{1}{1-\alpha}\ln\left(\sum_{i=1}^{N} p^\alpha(t_i)\right)$$

$$(\alpha \geq 0, \alpha \neq 1)$$

At a third step 14, a second set of data is collected. This second set of data related to the person's operation of the device at a second time.

At a fourth step 16, the second set of data is processed to establish a performance signature. The performance signature representing the person's performance in operating the device. The performance signature for comparing to the baseline signature to predict whether the person is/was experiencing an elevated cognitive load at the second time. In a first exemplary manner of processing the second set of data (measured in bits), an entropy signature is created according to Equation A. In a second exemplary manner of processing the second set of data (measured in bits), an entropy signature is created according to Equation B.

At a fifth step 18, the performance signature is compared to the baseline signature to predict (determine) whether the person is/was experiencing an elevated cognitive load at the second time. This comparison can include a determination of whether the performance signature is within or outside of a predesignated range, whether the performance signature is greater (or less) than the baseline signature, whether the difference between the performance signature and the baseline signature is within or outside a predesignated range, etc. It is preferred that the predesignated ranges come from analyzing the baseline signature versus the performance signature. An increased cognitive load increases the randomness of the data which is incorporated into the signature through the use of entropy, preferably Shannon entropy.

Figure 3:
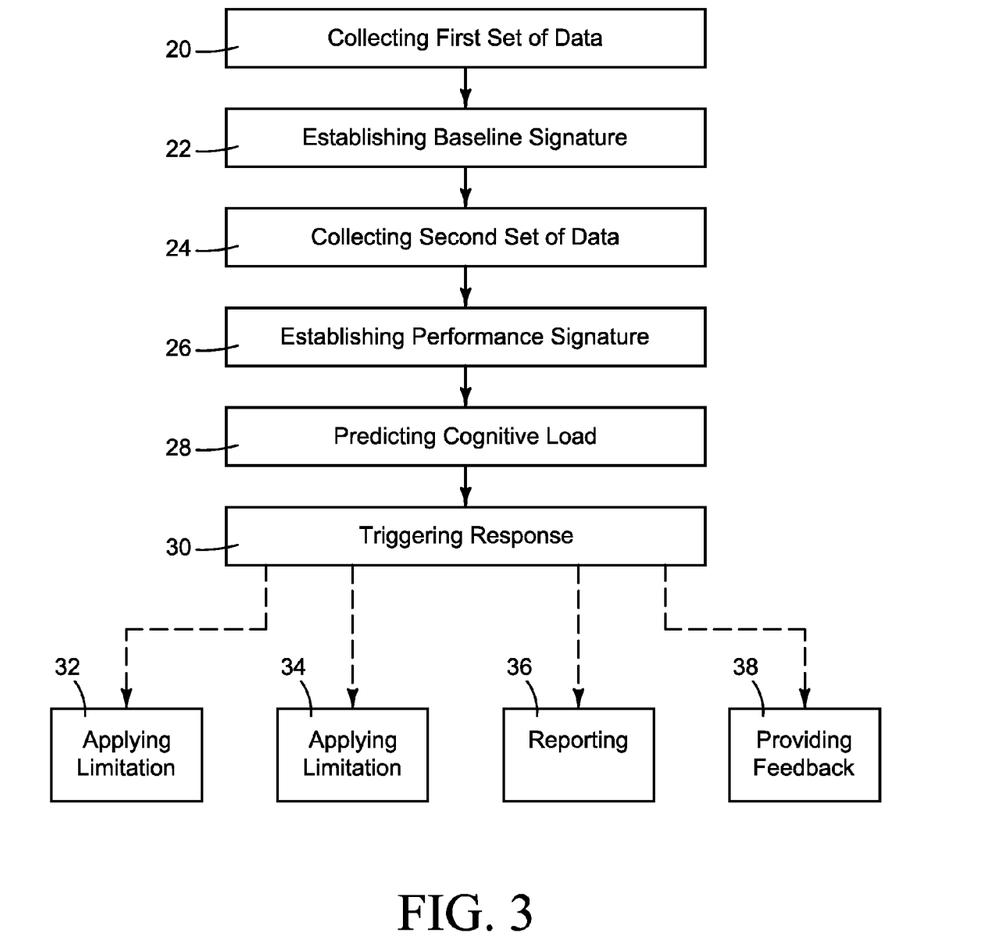
FIG. 3 is a flowchart illustrating a third exemplary method of determining if a person operating equipment is experiencing an elevated cognitive load.

Referring to FIG. 3, illustrated is another exemplary method of determining if a person operating equipment is experiencing an elevated cognitive load while using a device. The method comprising a series of steps.

At a first step 20, a first set of data is collected. This first set of data relating to the person's operation of the device itself. This first set of data for setting a baseline (control) against which the person's later performance is compared to determine if the person is experiencing an elevated cognitive load. Thus, it is preferred that the first step be performed at a first time when the person is known to not be experiencing an elevated cognitive load.

At a second step 22, the first set of data is processed to establish a baseline signature. This baseline signature representing the person's performance (use of the device) when not experiencing an elevated cognitive load. The baseline signature used as the baseline (control) against which the person's later performance (use of the device) is compared to determine if the person is experiencing an elevated cognitive load. In a first exemplary manner of processing the first set of data (measured in bits), the entropy signature is created according to the following equation ("Equation A"):

$$E = \sum_{i=1}^{N} p(t_i)\ln(p(t_i))$$

where N are all the possible values contained in the event stream (the number of bins used to form the histogram), and $p(t_i)$ is the estimated probability of a discrete event occurring. The binning process combines continuous events into discrete representations. In the case of this method, the number of bins can be adjusted to produce an optimal estimate of entropy.

In a second exemplary manner of processing the first set of data (measured in bits), the entropy signature is created according to the following equation ("Equation B"):

$$E_\alpha = \frac{1}{1-\alpha}\ln\left(\sum_{i=1}^{N} p^\alpha(t_i)\right)$$

$$(\alpha \geq 0, \alpha \neq 1)$$

At a third step 24, a second set of data is collected. This second set of data related to the person's operation of the device at a second time.

At a fourth step 26, the second set of data is processed to establish a performance signature. The performance signature representing the person's performance in operating the device. The performance signature for comparing to the baseline signature to predict whether the person was experiencing an elevated cognitive load at the second time. In a first exemplary manner of processing the second set of data (measured in bits), an entropy signature is created according to Equation A. In a second exemplary manner of processing the second set of data (measured in bits), an entropy signature is created according to Equation B.

At a fifth step 28, the performance signature is compared to the baseline signature to predict whether the person was experiencing an elevated cognitive load at the second time. This comparison can include a determination of whether the performance signature is within or outside of a predesignated range, whether the performance signature is greater (or less) than the baseline signature, whether the difference between the performance signature and the baseline signature is within or outside a predesignated range, etc.

At a sixth step 30, if the person is determined (in the fifth step 28) to be experiencing an elevated cognitive load, a response is triggered. In an optional step 32, a first exemplary response comprises applying a limitation to the person's use of the device. In an optional step 34, a second exemplary response comprises applying a limitation to the person's use of the equipment. In an optional step 36, a third exemplary response comprises reporting that the person was experiencing an elevated cognitive load while operating the device and/or equipment at the second time. In an optional step 38, a fourth exemplary response comprises providing feedback to the person regarding the existence of an elevated cognitive load. One or more of these optional steps can be taken alone or in combination with one another.

Figure 4:
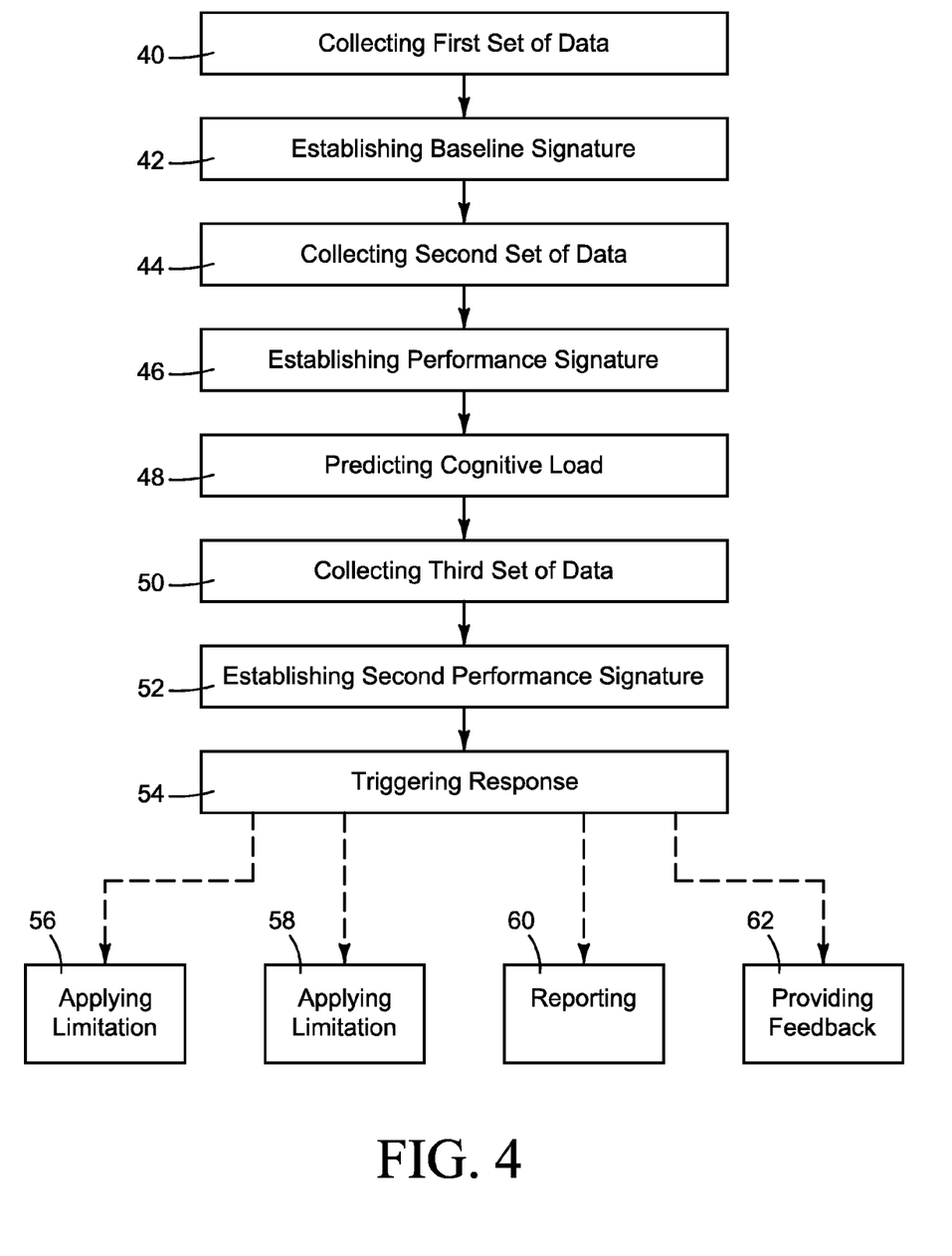
FIG. 4 is a flowchart illustrating a fourth exemplary method of determining if a person operating equipment is experiencing an elevated cognitive load.

Referring to FIG. 4, illustrated is another exemplary method of determining if a person operating equipment is experiencing an elevated cognitive load while using a device. The method comprising a series of steps.

At a first step 40, a first set of data is collected. This first set of data relating to the person's operation of the device itself. This first set of data for setting a baseline or control against which the person's later performance is compared to determine if the person is experiencing an elevated cognitive load. Thus, it is preferred that the first step be performed at a first time when the person is known to not be experiencing an elevated cognitive load.

At a second step 42, the first set of data is processed to establish a baseline signature. This baseline signature representing the person's performance (use of the device) when not experiencing an elevated cognitive load. The baseline signature used as the baseline (control) against which the person's later performance (use of the device) is compared to determine if the person is experiencing an elevated cognitive load. In one exemplary manner of processing the first set of data (measured in bits), the entropy signature is created according to the following equation ("Equation A"):

$$E = \sum_{i=1}^{N} p(t_i) \ln(p(t_i))$$

where N are all the possible values contained in the event stream (the number of bins used to form the histogram), and $p(t_i)$ is the estimated probability of a discrete event occurring. The binning process combines continuous events into discrete representations. In the case of this method, the number of bins can be adjusted to produce an optimal estimate of entropy.

In a second exemplary manner of processing the first set of data (measured in bits), the entropy signature is created according to the following equation ("Equation B"):

$$E_\alpha = \frac{1}{1-\alpha} \ln\left(\sum_{i=1}^{N} p^\alpha(t_i)\right)$$

$$(\alpha \geq 0, \alpha \neq 1)$$

At a third step 44, a second set of data is collected. This second set of data related to the person's operation of the device at a second time.

At a fourth step 46, the second set of data is processed to establish a performance signature. The performance signature representing the person's performance in operating the device. The performance signature for comparing to the baseline signature to predict whether the person was experiencing an elevated cognitive load at the second time. In a first exemplary manner of processing the second set of data (measured in bits), an entropy signature is created according to Equation A. In a second exemplary manner of processing the second set of data (measured in bits), an entropy signature is created according to Equation B.

At a fifth step 48, the performance signature is compared to the baseline signature to predict (determine) whether the person is experiencing an elevated cognitive load at the second time. This comparison can include a determination of whether the performance signature is within or outside of a predesignated range, whether the performance signature is greater (or less) than the baseline signature, whether the difference between the performance signature and the baseline signature is within or outside a predesignated range, etc.

At a sixth step 50, a third set of data is collected from a motion detector.

At a seventh step 52, the third set of data is processed to establish a second performance signature. The second performance signature relating to the relative motion of the person, the device, the equipment, and/or an object. For instance, the data could relate to whether or not the person is moving (or has been moving). While the determination that the person is moving could alone (without determining whether the person is experiencing an elevated cognitive load) be utilized to triggered a response, that approach is disfavored because it fails to accommodate the use by a second person (who is not operating the equipment (e.g., vehicle) of the device.

Alternatively, the motion detector data could be utilized to determine and/or predict the type of motion. For instance, whether the data represents motion associated with travel via automobile, rail, air, boat, bus, etc. In an exemplary method, the second performance signature comprises data only from automobile travel (e.g., data indicating that the person was travelling via rail would be excluded from the method).

At an eighth step 54, if the person is determined (in the fifth step 48) to be experiencing an elevated cognitive load, and the person is determined (in the seventh step 52) to be in motion, a response is triggered. Such a step, in the context of the person utilizing a messaging device while in an automobile, allows the method to distinguish between a driver of the automobile (who would have an elevated cognitive load) and a passenger (who would likely not have an elevated cognitive load). The determination of whether a response is triggered could optionally take into consideration the type of motion (e.g., automobile, rail, air boat, bus).

In an optional step 56, a first exemplary response comprises applying a limitation to the person's use of the device. In an optional step 58, a second exemplary response comprises applying a limitation to the person's use of the equipment. In an optional step 60, a third exemplary response comprises reporting that the person was experiencing an elevated cognitive load while operating the device and/or equipment at the second time. In an optional step 62, a fourth exemplary response comprises providing feedback to the person regarding the existence of an elevated cognitive load. One or more of these optional steps can be taken.

Figure 5:
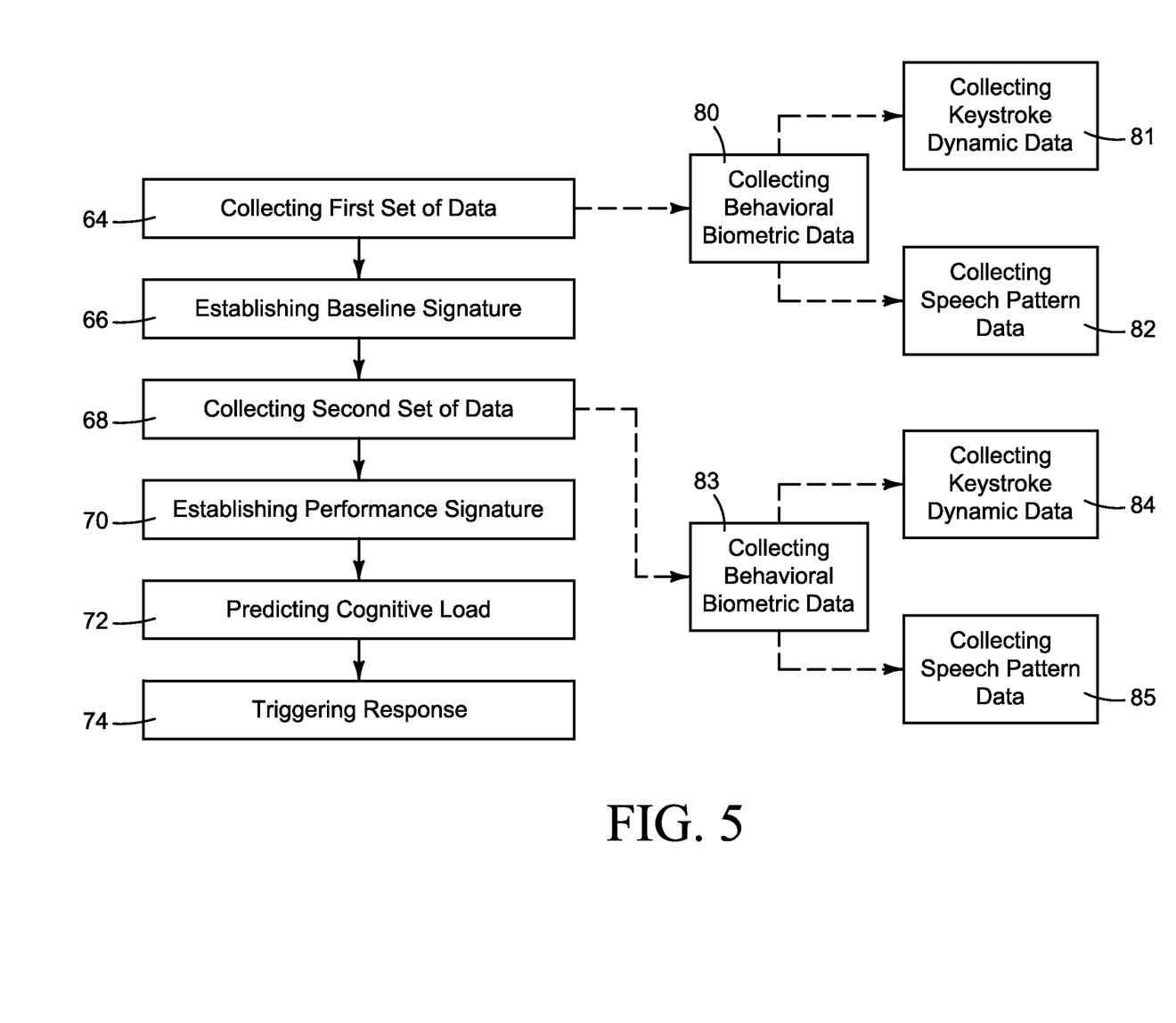
FIG. 5 is a flowchart illustrating a fifth exemplary method of determining if a person operating equipment is experiencing an elevated cognitive load.

Referring to FIG. 5, illustrated is another exemplary method of determining if a person operating equipment is experiencing an elevated cognitive load while using a device. The method comprising a series of steps.

At a first step 64, a first set of data is collected. This first set of data relating to the person's operation of the device itself. This first set of data for setting a baseline (control) against which the person's later performance is compared to determine if the person is experiencing an elevated cognitive load. Thus, it is preferred that the first step be performed at a first time when the person is known to not be experiencing an elevated cognitive load.

At a second step 66, the first set of data is processed to establish a baseline signature. This baseline signature representing the person's performance (use of the device) when not experiencing an elevated cognitive load. The baseline signature used as the baseline (control) against which the person's later performance (use of the device) is compared to determine if the person is experiencing an elevated cognitive load. In one exemplary manner of processing the first set of data (measured in bits), the entropy signature is created according to the following equation ("Equation A"):

$$E = \sum_{i=1}^{N} p(t_i)\ln(p(t_i))$$

where N are all the possible values contained in the event stream (the number of bins used to form the histogram), and $p(t_i)$ is the estimated probability of a discrete event occurring. The binning process combines continuous events into discrete representations. In the case of this method, the number of bins can be adjusted to produce an optimal estimate of entropy.

In a second exemplary manner of processing the first set of data (measured in bits), the entropy signature is created according to the following equation ("Equation B"):

$$E_\alpha = \frac{1}{1-\alpha}\ln\left(\sum_{i=1}^{N} p^\alpha(t_i)\right)$$

$$(\alpha \geq 0, \alpha \neq 1)$$

At a third step 68, a second set of data is collected. This second set of data related to the person's operation of the device at a second time.

At a fourth step 70, the second set of data is processed to establish a performance signature. The performance signature representing the person's performance in operating the device. The performance signature for comparing to the baseline signature to predict whether the person was experiencing an elevated cognitive load at the second time. In a first exemplary manner of processing the second set of data (measured in bits), an entropy signature is created according to Equation A. In a second exemplary manner of processing the second set of data (measured in bits), an entropy signature is created according to Equation B.

At a fifth step 72, the performance signature is compared to the baseline signature to predict (determine) whether the person was experiencing an elevated cognitive load at the second time. This comparison can include a determination of whether the performance signature is within or outside of a predesignated range, whether the performance signature is greater (or less) than the baseline signature, whether the difference between the performance signature and the baseline signature is within or outside a predesignated range, etc.

At a sixth step 74, if the person is determined (in the fifth step 72) to be experiencing an elevated cognitive load, a response is triggered. In an optional step 80, the first set of data comprises behavioral biometric data relating to the person's operation of the device. In an optional step 81, the first set of data comprises behavioral biometric data relating to the person's operation of the device, namely logging keystroke dynamic data related to the person's operation of the device where the device has an input device (e.g., keyboard, touch screen, mouse) which is utilized by the person. In an optional step 82, the first set of data comprises behavioral biometric data relating to the person's speech patterns (e.g., rate of speaking, nature of speaking) related to the person's operation of the device. In an optional step 83, the second set of data comprises behavioral biometric data relating to the person's operation of the device. In an optional step 84, the second set of data comprises behavioral biometric data relating to the person's operation of the device, namely logging keystroke dynamic data related to the person's operation of the device where the device has an input device (e.g., keyboard, touch screen, mouse) which is utilized by the person. In an optional step 85, the second set of data comprises behavioral biometric data relating to the person's speech patterns related to the person's operation of the device. One or more of these optional steps can be taken alone or in combination with one another.

Alternatively, the use of the equipment can be monitored to determine if distracted operation is taking place (e.g., the person operating equipment is experiencing an elevated cognitive load while operating the equipment).

In one exemplary method, conditions are established based upon entropy values derived from statistical analytical review of a preselected number of conditions that create a parameter threshold and determining if the entropy value falls within or without a selected set of characteristics.

In another exemplary method, the method is implemented within the constructs of a device (e.g., a wireless messaging device) being operated by a person.

Exemplary apparatuses could be used or enhanced by communication with current or future systems installed within a vehicle. Such systems could assist in verifying if the person was the operator of the vehicle, or the proximity of the apparatus to the driver's cockpit of the vehicle, thereby enhancing the reliability of the signature obtained.

Exemplary methods/apparatuses described herein can be utilized to help identify a distracted driver where appropriate action may then be taken by the driver or others to allow the driver to refocus fully on driving the vehicle.

Apparatuses utilized to determine if a person operating equipment is experiencing an elevated cognitive load are also described. An exemplary apparatus comprises a cell phone programmed to rapidly detect and quantify the cognitive distraction of the user by analyzing keystroke dynamics.

Figure 6:
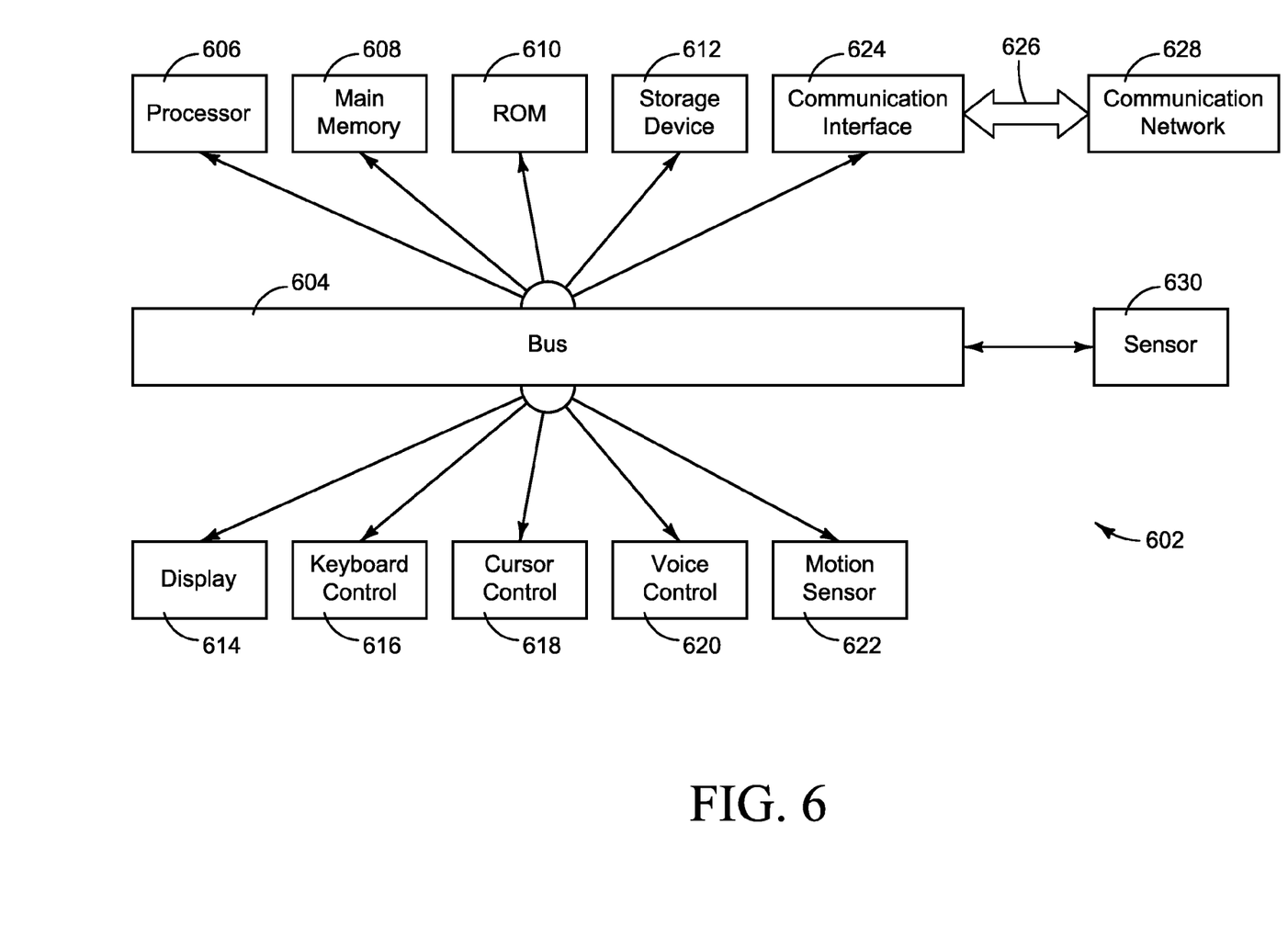
FIG. 6 is a block diagram of an exemplary device implementing a method of determining if a person operating equipment is experiencing an elevated cognitive load.

A first exemplary apparatus implementing a method of determining if a person operating equipment is experiencing an elevated cognitive load is illustrated in FIG. 6. FIG. 6 illustrates a messaging device 602. The messaging device 602 includes a bus 604 or other communication mechanism for communicating information, and a processor 606 coupled with the bus 604 for processing the information.

The messaging device 602 also includes main memory 608, such as a random access memory (RAM) or other dynamic storage device (e.g., dynamic RAM (DRAM), static RAM (SRAM), synchronous DRAM (SDRAM), flash RAM), coupled to the bus 604 for storing information and instructions to be executed by processor 606. In addition, main memory 608 may be used for storing temporary variables or other intermediate information during execution of instructions to be executed by processor 606.

The messaging device 602 further includes a read only memory (ROM) 610 or other static storage device (e.g., programmable ROM (PROM), erasable PROM (EPROM), and electrically erasable PROM (EEPROM)) coupled to bus 604 for storing static information and instructions for processor 606. A storage device 612, such as a magnetic disk or optical disk, may be provided and coupled to bus 604 for storing information and instructions.

The messaging device 602 may be coupled via bus 604 to a display 614 (e.g., liquid crystal display (LCD), light emitting diode (LED) display, voice synthesis hardware, voice synthesis software) for displaying and/or providing information to a user of the messaging device 602.

The messaging device 602 may include one or more input devices for communicating information and command selections to processor 606. Examples of input devices include, but are not limited to, keyboard control 616, cursor control 618, voice control 620, and motion sensor 622.

The keyboard control 616 can comprise physical keys (e.g., a keyboard) and/or "virtual" keys (e.g., displayed on a touch screen display).

The cursor control 618 for communicating direction information and command selections to processor 606, and for controlling cursor movement on the display 614. Examples of cursor controls 618 include, but are not limited to, a mouse, a trackball, cursor direction keys, touch screen display, optical character recognition hardware, and optical character recognition hardware. Command selections can be also be implemented via the voice control 620 (e.g., voice recognition hardware, voice recognition software). The motion sensor 622 for communicating information regarding the relative motion of a person, device, equipment, and/or object to processor 606.

The messaging device 602 performs a portion of, or all of, the processing steps of the exemplary method(s) in response to processor 606 executing one or more sequences of one or more instructions contained in a memory, such as the main memory 608. Such instructions may be read into the main memory 608 from another computer readable medium, such as storage device 612. One or more processors in a multi-processing arrangement may also be employed to execute the sequences of instructions contained in main memory 608. In other exemplary systems, hard-wired circuitry may be used in place of, or in combination with, software instructions. Thus, exemplary systems are not limited to any specific combination of hardware circuitry and software.

As stated above, the messaging device 602 includes at least one computer readable medium or memory programmed according to an exemplary method, and for containing data structures, tables, records, or other data described herein. The messaging device 602 includes software for controlling the messaging device 602, and for enabling the messaging device 602 to interact with a human user. Such software may include, but is not limited to, device drivers, operating systems, development tools, and applications software. Various forms of computer readable media may be involved in carrying out one or more sequences of one or more instructions to processor 606 for execution.

The messaging device 602 also includes a communication interface 624 coupled to bus 604. Communication interface 624 sends and receives electrical, electromagnetic or optical signals that carry digital data streams representing various types of information (e.g., messages) via a network link 626 to a communication network 628. Examples of communications networks include, but are not limited to, local area networks (LAN), wide area networks (WAN), intranet, extranet, global communication networks, the Internet, wireless communication networks, wired communication networks, Bluetooth® network connections, RF network connections, and IR network connections.

The messaging device 602 may also include one or more sensors 630 for sensing and communicating information via the bus 604 to the processor 606.

One exemplary messaging device 602 comprising a cellular telephone having a display 614 and a keyboard control 616. The messaging device 602 configured for sending and receiving text messages via the communication interface 624 which connects to a communication network 628 via the network link 626.

The cellular telephone having one or more sensors 630 for logging behavioral biometric data relating to a user's use of the messaging device 602. The sensor 630 could comprise hardware or software for logging behavioral biometric data related to the user's operation of the messaging device 602 and utilization of one or more of the input devices connected to the messaging device 602.

For instance, the sensor 630 could log keystroke dynamic data compiled from monitoring the user's use of the keyboard control 616. The keystroke dynamic data could include information regarding key events. The term "key event" means "information regarding depression and release of keys on a keyboard control 616," unless the context clearly dictates otherwise. Key events for letters, numbers, spaces, backspaces, and/or punctuation characters (e.g., comma, period, question mark) can be logged. The key events can include information including (but not limited to): timestamp, event type (e.g., key up, key down), and the identity of the key depressed (or released). This keystroke dynamic data could be stored (via main memory 608) or immediately processed by processor 606.

In another example, the sensor 630 could log data regarding the user's speech patterns (via voice control 620).

The sensor 630 collecting a first set of data at a first time, for instance the keystroke dynamic data discussed above. This first set of data processed via the processor 606 to establish a baseline signature. This baseline signature preferably stored in the main memory 608. The baseline signature representing the user's performance (use of the messaging device 602) when not experiencing an elevated cognitive load. At a later time, a second set of data (such as the keystroke dynamic data discussed above) is collected by the sensor 630. This second set of data related to the person's operation of the device at the second time. This second set of data processed by the processor 606 to establish a performance signature. The performance signature representing the user's performance at the second time. The processor 606 then compares the performance signature to the baseline signature. Based upon the output or results of the comparison, the processor 606 predicts whether the user, at the second time, was experiencing an elevated cognitive load.

If the processor 606 determines that the user is experiencing an elevated cognitive load, a response is triggered. One example of such a response comprises the disabling of the communication interface 624 thereby preventing further use by the user of the messaging device 602 for sending messages.

One exemplary computer-readable storage medium storing one or more sequences of instructions which, when executed by one or more processors, causes the one or more processors to perform a method of determining if a person operating equipment is experiencing an elevated cognitive load, comprises a number of steps: collecting a first set of data related to the person's operation of a device at a first time when the person is not experiencing an elevated cognitive load; processing the first set of data to establish a baseline signature; collecting a second set of data related to the person's operation of the device at a second time; processing the second set of data to establish a performance signature; comparing the performance signature to the baseline signature to determine whether the person is experiencing an elevated cognitive load at the second time; and triggering a response if the person is experiencing an elevated cognitive load. Optionally, the response is selected from the group consisting of applying a limitation to the person's use of the device, reporting that the person was experiencing an elevated cognitive load while operating the device at the second time, and providing feedback to the person regarding the existence of an elevated cognitive load while operating the device at the second time. Optionally, the method further comprises the steps of: collecting a third set of data from a motion detector; processing the third set of data to establish a second performance signature, wherein the second performance signature relates to movement; and triggering a response if the person is experiencing an elevated cognitive load, and the second performance signature indicates the person is moving.

One exemplary computer-implemented method of determining if a person operating a device is experiencing an elevated cognitive load comprising a number of steps. At a first step, a sensor measures behavioral biometric data relating to the person's operation of a device to collect a first set of data related to the person's operation of the device at a first time when the person is not experiencing an elevated cognitive load. At a second step, a computer-readable storage medium stores the first set of data. At a third step, a processor processes the first set of data to establish a baseline signature. A forth step, a sensor measures behavioral biometric data relating to the person's operation of the device to collect a second set of data related to the person's operation of the device at a second time. This sensor could be the same sensor in the first step, or a second sensor. At a fifth step, a computer-readable storage medium stores the second set of data. This storage medium could be the same storage medium in the second step, or could be a second storage medium. At a sixth step, a processor processes the second set of data to establish a performance signature. This processor could be the same processor in the third step, or a second processor. At a seventh step, a processor compares the performance signature to the baseline signature to determine whether the person is experiencing an elevated cognitive load at the second time. This processor could be the same processor as in one or more of the earlier steps, or a separate processor. At an eighth step, a processor triggers a response if the person is experiencing an elevated cognitive load. This processor could be the same processor as in one or more of the earlier steps, or a separate processor. Alternatively, the device is a messaging device, and the measurement of behavioral biometric data comprises measuring keystroke dynamic data related to the person's operation of the messaging device.

Any suitable structure and/or material can be used for the exemplary apparatuses, and a skilled artisan will be able to select an appropriate structure and material for an exemplary apparatus in a particular embodiment based on various considerations, including the intended use of the exemplary apparatus, the intended arena within which the exemplary apparatus will be used, and the equipment and/or accessories with which the exemplary apparatus is intended to be used, among other considerations.

It is noted that all steps, structure and features of the various described and illustrated exemplary methods and apparatuses can be combined in any suitable configuration for inclusion in an exemplary method and/or exemplary apparatus according to a particular embodiment. For example, a method according a particular embodiment can include neither, one, or both of the steps of triggering a response, and collecting a third set of data from a motion detector.

The foregoing detailed description provides exemplary embodiments of the invention and includes the best mode for practicing the invention. The description and illustration of these embodiments is intended only to provide examples of the invention, and not to limit the scope of the invention, or its protection, in any manner.

What is claimed is:

1. A method of determining if a person operating equipment is experiencing an elevated cognitive load, said method comprising the steps of:
collecting a first set of data related to the person's operation of a device at a first time;
processing said first set of data to establish a baseline signature, wherein the step of processing said first set of data to establish a baseline signature comprises the equation $$E = \sum_{i=1}^{N} p(t_i)\ln(p(t_i))$$

or the equation $$E_\alpha = \frac{1}{1-\alpha}\ln\left(\sum_{i=1}^{N} p^\alpha(t_i)\right)$$

$(\alpha \geq 0, \alpha \neq 1);$ collecting a second set of data related to the person's operation of the device at a second time;
processing said second set of data to establish a performance signature; and
comparing said performance signature to said baseline signature to determine whether the person is experiencing an elevated cognitive load at said second time.

2. The method of claim 1, further comprising the step of triggering a response if said person is experiencing an elevated cognitive load.

3. The method of claim 2, wherein said response is applying a limitation to the person's use of the device.

4. The method of claim 2, wherein said response is reporting that said person was experiencing an elevated cognitive load while operating said device at said second time.

5. The method of claim 2, wherein said response is providing feedback to said person regarding the existence of an elevated cognitive load while operating said device at said second time.

6. The method of claim 1, further comprising the steps of:
collecting a third set of data related to the relative motion of the person from a motion detector; and
processing said third set of data to establish a second performance signature, wherein said second performance signature relates to the person's relative motion.

7. The method of claim 6, further comprising the step of triggering a response if said person is experiencing an elevated cognitive load, and said second performance signature indicates said person is moving.

8. The method of claim 1, wherein the step of collecting a first set of data related to the person's operation of the device at a first time is performed when the person is not experiencing an elevated cognitive load.

9. The method of claim 1, wherein said steps of collecting a first set of data and collecting a second set of data comprise measuring behavioral biometric data relating to the person's operation of said device.

10. The method of claim 9, wherein the measurement of behavioral biometric data comprises measuring keystroke dynamic data related to the person's operation of said device.

11. The method of claim 9, wherein said device is a messaging device.

12. The method of claim 9, wherein the measurement of behavioral biometric data comprises measuring the person's speech patterns related to the person's operation of said device.

13. The method of claim 1, wherein the step of processing said second set of data to establish a performance signature comprises the equation $$E = \sum_{i=1}^{N} p(t_i) \ln(p(t_i))$$

or the equation $$E_\alpha = \frac{1}{1-\alpha} \ln\left(\sum_{i=1}^{N} p^\alpha(t_i)\right)$$

$(\alpha \geq 0, \alpha \neq 1)$.

14. The method of claim 1, further comprising the step of triggering a response if said person is experiencing an elevated cognitive load; and wherein the steps of collecting a first set of data and collecting a second set of data comprise measuring behavioral biometric data relating to the person's operation of said device, and further wherein the measurement of behavioral biometric data comprises measuring keystroke dynamic data related to the person's operation of said device.

15. A non-transitory computer-readable storage medium storing one or more sequences of instructions which, when executed by one or more processors, causes the one or more processors to perform a method of determining if a person operating equipment is experiencing an elevated cognitive load, said method comprising the steps of:

collecting a first set of data related to the person's operation of a device at a first time when the person is not experiencing an elevated cognitive load;

processing said first set of data to establish a baseline signature, wherein the step of processing said first set of data to establish a baseline signature comprises the equation $$E = \sum_{i=1}^{N} p(t_i) \ln(p(t_i))$$

or the equation $$E_\alpha = \frac{1}{1-\alpha} \ln\left(\sum_{i=1}^{N} p^\alpha(t_i)\right)$$

$(\alpha \geq 0, \alpha \neq 1)$;

collecting a second set of data related to the person's operation of the device at a second time;

processing said second set of data to establish a performance signature;

comparing said performance signature to said baseline signature to determine whether the person is experiencing an elevated cognitive load at said second time; and triggering a response if said person is experiencing an elevated cognitive load.

16. The method of claim 15, wherein said response is selected from the group consisting of applying a limitation to the person's use of the device, reporting that said person was experiencing an elevated cognitive load while operating said device at said second time, and providing feedback to said person regarding the existence of an elevated cognitive load while operating said device at said second time.

17. The method of claim 16, further comprising the steps of:

collecting a third set of data from a motion detector;

processing said third set of data to establish a second performance signature, wherein said second performance signature relates to movement; and triggering a response if said person is experiencing an elevated cognitive load, and said second performance signature indicates said person is moving.

18. A computer-implemented method of determining if a person operating a device is experiencing an elevated cognitive load, said method comprising the steps of:

a sensor measuring behavioral biometric data relating to the person's operation of a device to collect a first set of data related to the person's operation of said device at a first time when the person is not experiencing an elevated cognitive load;

a non-transitory computer-readable storage medium storing said first set of data;

a processor processing said first set of data to establish a baseline signature according to the equation $$E = \sum_{i=1}^{N} p(t_i) \ln(p(t_i))$$

or the equation $$E_\alpha = \frac{1}{1-\alpha} \ln\left(\sum_{i=1}^{N} p^\alpha(t_i)\right)$$

$(\alpha \geq 0, \alpha \neq 1)$;

said sensor measuring behavioral biometric data relating to the person's operation of said device to collect a second set of data related to the person's operation of the device at a second time;

said non-transitory computer-readable storage medium storing said second set of data;

said processor processing said second set of data to establish a performance signature;

said processor comparing said performance signature to said baseline signature to determine whether the person is experiencing an elevated cognitive load at said second time; and said processor triggering a response if said person is experiencing an elevated cognitive load.

19. The computer-implemented method of claim 18, wherein said device is a messaging device, and the measurement of behavioral biometric data comprises measuring keystroke dynamic data related to the person's operation of said messaging device.

20. The computer-implemented method of claim 18, wherein the step of processing said second set of data to establish a performance signature comprises the equation $$E = \sum_{i=1}^{N} p(t_i)\ln(p(t_i))$$

or the equation $$E_\alpha = \frac{1}{1-\alpha}\ln\left(\sum_{i=1}^{N} p^\alpha(t_i)\right)$$

$(\alpha \geq 0, \alpha \neq 1).$

21. The method of claim 15, wherein the step of processing said second set of data to establish a performance signature comprises the equation $$E = \sum_{i=1}^{N} p(t_i)\ln(p(t_i))$$

or the equation $$E_\alpha = \frac{1}{1-\alpha}\ln\left(\sum_{i=1}^{N} p^\alpha(t_i)\right)$$

$(\alpha \geq 0, \alpha \neq 1).$

22. A method of determining if a person operating equipment is experiencing an elevated cognitive load, said method comprising the steps of:
   collecting a first set of data related to the person's operation of a device at a first time;
   processing said first set of data to establish a baseline signature;
   collecting a second set of data related to the person's operation of the device at a second time;
   processing said second set of data to establish a performance signature, wherein the step of processing said second set of data to establish a performance signature comprises using the equation $$E = \sum_{i=1}^{N} p(t_i)\ln(p(t_i))$$

or the equation $$E_\alpha = \frac{1}{1-\alpha}\ln\left(\sum_{i=1}^{N} p^\alpha(t_i)\right)$$

$(\alpha \geq 0, \alpha \neq 1);$ and
   comparing said performance signature to said baseline signature to determine whether the person is experiencing an elevated cognitive load at said second time.

23. The method of claim 22, wherein the step of processing said second set of data to establish a performance signature comprises the equation $$E = \sum_{i=1}^{N} p(t_i)\ln(p(t_i))$$

or the equation $$E_\alpha = \frac{1}{1-\alpha}\ln\left(\sum_{i=1}^{N} p^\alpha(t_i)\right)$$

$(\alpha \geq 0, \alpha \neq 1).$

24. A non-transitory computer-readable storage medium storing one or more sequences of instructions which, when executed by one or more processors, causes the one or more processors to perform a method of determining if a person operating equipment is experiencing an elevated cognitive load, said method comprising the steps of:
   collecting a first set of data related to the person's operation of a device at a first time when the person is not experiencing an elevated cognitive load;
   processing said first set of data to establish a baseline signature;
   collecting a second set of data related to the person's operation of the device at a second time;
   processing said second set of data to establish a performance signature, wherein the step of processing said second set of data to establish a performance signature comprises the equation $$E = \sum_{i=1}^{N} p(t_i)\ln(p(t_i))$$

or the equation $$E_\alpha = \frac{1}{1-\alpha}\ln\left(\sum_{i=1}^{N} p^\alpha(t_i)\right)$$

$(\alpha \geq 0, \alpha \neq 1);$ comparing said performance signature to said baseline signature to determine whether the person is experiencing an elevated cognitive load at said second time; and
   triggering a response if said person is experiencing an elevated cognitive load.

25. A computer-implemented method of determining if a person operating a device is experiencing an elevated cognitive load, said method comprising the steps of:
   a sensor measuring behavioral biometric data relating to the person's operation of a device to collect a first set of data related to the person's operation of said device at a first time when the person is not experiencing an elevated cognitive load;

a non-transitory computer-readable storage medium storing said first set of data;

a processor processing said first set of data to establish a baseline signature;

said sensor measuring behavioral biometric data relating to the person's operation of said device to collect a second set of data related to the person's operation of the device at a second time;

said non-transitory computer-readable storage medium storing said second set of data;

said processor processing said second set of data to establish a performance signature according to the equation $$E = \sum_{i=1}^{N} p(t_i)\ln(p(t_i))$$

or the equation $$E_\alpha = \frac{1}{1-\alpha}\ln\left(\sum_{i=1}^{N} p^\alpha(t_i)\right)$$

$(\alpha \geq 0, \alpha \neq 1)$;

said processor comparing said performance signature to said baseline signature to determine whether the person is experiencing an elevated cognitive load at said second time; and said processor triggering a response if said person is experiencing an elevated cognitive load.

* * * * *